(12) United States Patent
Galin

(10) Patent No.: US 6,171,337 B1
(45) Date of Patent: Jan. 9, 2001

(54) POSITIVE POWER ANTERIOR CHAMBER OCULAR IMPLANT

(76) Inventor: Miles A. Galin, 345 E. 37$^{th}$ St. - 3$^{rd}$ Fl., New York, NY (US) 10016

(*) Notice: Under 35 U.S.C. 154(b), the term of this patent shall be extended for 0 days.

(21) Appl. No.: 09/282,476

(22) Filed: Mar. 31, 1999

(51) Int. Cl.$^7$ .................................................. A61F 2/16
(52) U.S. Cl. .................................. 623/6.11; 623/6.38
(58) Field of Search .................................. 623/6.11, 6.38, 623/6.4, 6.42, 6.31

(56) References Cited

U.S. PATENT DOCUMENTS

| | | |
|---|---|---|
| Re. 31,963 | 8/1985 | Kelman . |
| 4,268,921 | 5/1981 | Kelman . |
| 4,296,501 | 10/1981 | Kelman . |
| 4,340,979 | 7/1982 | Kelman . |
| 4,343,050 | 8/1982 | Kelman . |
| 4,370,760 | 2/1983 | Kelman . |
| 4,403,353 | 9/1983 | Tennant . |
| 4,404,694 | 9/1983 | Kelman . |
| 4,442,553 | 4/1984 | Hessburg . |
| 4,451,938 | 6/1984 | Kelman . |
| 4,463,457 | 8/1984 | Kelman . |
| 4,477,931 | 10/1984 | Kelman . |
| 4,495,665 | 1/1985 | Kelman . |
| 4,508,216 | 4/1985 | Kelman . |
| 4,524,468 | 6/1985 | Kelman . |
| 4,530,117 | 7/1985 | Kelman . |
| 4,534,069 | 8/1985 | Kelman . |

(List continued on next page.)

OTHER PUBLICATIONS

Colin, et al. Refractive and Corneal Surgery 6:245–251 (1990).

Baikoff, et al. Refractive and Corneal Surgery 6:252–260 (1990).

Ophthalmology Alert 1(11):41–42 & Comment (Nov. 1990).

Apple, et al., In Intraocular Lenses: Evolution, Designs, Complications & Pathology (William & Wilkens, Baltimore) Chapter 4, pp. 59–105 (1989).

Apple, et al., In Intraocular Lenses: Evolution, Designs, Complications & Pathology (William & Wilkens, Baltimore) Chapter 3, pp. 45–58 (1989).

Perez–Santonja, et al., J. Cataract–Refract. and Surg. 22:183–187 (1986).

Kaufman, et al., J. Cataract–Refract. Surg. 23:815 (Jul./Aug. 1997).

Perez–Santonja, et al., J. Cataract–Refract. Surg. 23:816–817 (Jul./Aug. 1997).

Apple, et al., J. Cataract–Refract. Surg. 13:157–189 (Mar. 1987).

*Primary Examiner*—Dinh X. Nguyen
(74) *Attorney, Agent, or Firm*—Baker Botts LLP

(57) ABSTRACT

The disclosure is directed to a positive power anterior chamber ocular implant for placement in a phakic eye to correct refractive errors caused by hyperopia which includes at least one convex surface and means for positioning the lens in the anterior chamber of an eye, wherein contact between the lens and other anatomic bodies such as the anatomical lens, the corneal endothelium and iris is avoided, and wherein the means for positioning avoids contact with the iris. The disclosure is further directed to a method of preparing such an implant and a method of correcting refractive errors caused by hyperopia in a patient in need thereof comprising surgically implanting and anchoring in the anterior chamber of a phakic eye a positive power anterior chamber ocular implant comprising a positive artificial refracting lens having at least one convex surface and a means for positioning the lens in the anterior chamber of the eye, wherein contact between the positive refracting lens and other anatomic bodies is avoided and wherein the means for positioning the lens avoids contact with the iris.

10 Claims, 1 Drawing Sheet

U.S. PATENT DOCUMENTS

| | | |
|---|---|---|
| 4,538,611 | 9/1985 | Kelman . |
| 4,576,607 | 3/1986 | Kelman . |
| 4,586,930 | 5/1986 | Kelman . |
| 4,591,358 | 5/1986 | Kelman . |
| 4,596,578 | 6/1986 | Kelman . |
| 4,601,722 | 7/1986 | Kelman . |
| 4,605,409 | 8/1986 | Kelman . |
| 4,608,049 | 8/1986 | Kelman . |
| 4,648,878 | 3/1987 | Kelman . |
| 4,648,879 | 3/1987 | Kelman . |
| 4,664,667 | 5/1987 | Kelman . |
| 4,676,792 | 6/1987 | Praeger . |
| 4,676,794 | 6/1987 | Kelman . |
| 4,678,469 | 7/1987 | Kelman . |
| 4,710,194 | 12/1987 | Kelman . |
| 4,769,035 | 9/1988 | Kelman . |
| 4,781,719 | 11/1988 | Kelman . |
| 4,791,924 | 12/1988 | Kelman . |
| 4,808,181 | 2/1989 | Kelman . |
| 4,828,558 | 5/1989 | Kelman . |
| 4,833,890 | 5/1989 | Kelman . |
| 4,863,465 | 9/1989 | Kelman . |
| 4,871,363 | 10/1989 | Kelman . |
| 4,911,715 | 3/1990 | Kelman . |
| 4,932,971 | 6/1990 | Kelman . |
| 4,950,288 | 8/1990 | Kelman . |
| 4,955,902 | 9/1990 | Kelman . |
| 5,071,432 | 12/1991 | Baikoff . |
| 5,074,876 | 12/1991 | Kelman . |
| 5,192,319 | 3/1993 | Worst . |
| 5,476,515 | 12/1995 | Kelman et al. . |
| 5,489,299 | 2/1996 | Schachar . |
| 5,628,798 | 5/1997 | Eggleston et al. . |
| 5,652,014 | 7/1997 | Galin et al. . |

POSITIVE POWER ANTERIOR CHAMBER OCULAR IMPLANT

FIELD OF THE INVENTION

This invention relates to a positive power anterior chamber ocular implant for placement in a phakic eye to correct refractive errors such as hyperopia, hyperopic or mixed astigmatism, a method for treating hyperopia in a patient in need thereof comprising surgically implanting and anchoring in the anterior chamber angle of a phakic eye a positive power anterior chamber ocular implant comprising a positive artificial refracting lens having at least one convex surface and a means for positioning the lens in the anterior chamber of the eye, wherein contact between the positive refracting lens and other anatomic bodies is avoided and wherein the means for positioning the lens avoids contact with the iris.

BACKGROUND OF THE INVENTION

It is well known to those skilled in the art that intraocular lenses are predominantly designed to replace a previously or simultaneously removed lens in a cataract patient (see, for example, U.S. Pat. No. 5,628,798). However, although the implantation of intraocular lenses has constituted an appreciable surgical advance, such implantation has been known to cause immediate or latent damage to the corneal endothelium, immediate or latent inflammatory responses in the anterior and/or posterior segments of the eye, immediate or latent secondary fibrosis and/or neovascularization, and other problems.

Intraocular lenses have been surgically implanted into an aphakic eye in order to take the place of the natural lens. (See, U.S. Pat. No. 2,834,023). Intraocular lenses have been implanted into the posterior chamber of the phakic eye, i.e., an eye having a natural lens in situ, to compensate for refractive errors or to create a specific refraction to assist in visual function. (See, U.S. Pat. No. 4,769,035).

Certain difficulties are associated with implanting an intraocular lens in the phakic eye that are not encountered when implanting a lens in the aphakic eye. The phakic eye is a substantially more reactive environment than the aphakic eye. Inflammatory reactions tend to be greater in the phakic eye resulting in a concomitant increase in damage to the eye caused by implanting intraocular lenses. One reason is that in the aphakic eye, the natural lens does not pull on the highly reactive ciliary body thus, the ciliary body is in a "resting state" and tends to undergo some degree of atrophy. Additionally, the presence of the natural lens in the phakic eye crowds the area in which an intraocular implant can be placed in the eye.

Placements of intraocular lenses in the posterior chamber of the phakic eye also have been known to cause cataract formation in the natural lens that remains in situ due to contact between the implant and the natural lens. In contrast, implanting intraocular lenses in patients having cataract removal cannot induce such an effect since the natural lens has been removed.

The anterior chamber of an eye is that area in front of the iris and behind the cornea. The iris acts as a divider between the anterior chamber and the posterior chamber. The anterior chamber was originally studied as a preferred location for aphakic intraocular implants particularly when no posterior capsule was present. However, significant drawbacks were discovered.

The phakic eye has a shallower anterior chamber (i.e., the average antero-posterior depth is less) than the aphakic eye, and the iris is in contact with the anatomic lens. Therefore, if an inflammatory reaction occurs in the phakic eye, there can be adherence of the iris to the anterior surface of the anatomic lens. Furthermore, if posterior chamber implants were to cause an inflammatory reaction in the phakic eye, cataract formation may occur in the natural lens which remains in situ.

For intraocular lenses implantation, it was known in the art that the preferred location of the implant was in the posterior chamber, i.e., that area behind the iris and in front of the natural lens in situ. Intraocular implants for the posterior chamber have been designed to treat myopia (nearsightedness) and hyperopia (farsightedness).

However, a drawback existed for correcting refractive errors in patients with high myopia, extreme nearsightedness, with posterior chamber ocular lenses. Because of the high degree of corrective refraction of the optic, which causes the optical zone to be quite small, a myopic posterior chamber lens may irritate the iris and potentially touch the natural lens. Anterior chamber intraocular lenses for high myopia were explored for implantation in the phakic eye which would not be in contact with uveal tissue or the human lens. Hyperopic posterior lenses would not cause similar damage because the edge of a hyperopic lens is thinner and does not project the peripheral iris forward. In addition, the vault of a hyperopic posterior lens prevents human lens touch. Therefore, there is no incentive to place a hyperopic lens into the anterior chamber.

U.S. Pat. No. 4,676,792 discloses an uncoated minus power anterior chamber implant for the treatment of myopia. Uncoated minus power implants have been used in patients having high myopia that is not satisfactorily corrected with spectacles or contact lenses (see, for example, Colin et al., 1990, Refractive and Corneal Surgery 6:245–251 and Baikoff et al., 1990, Refractive and Corneal Surgery 6:252–260). The prior art does not disclose implanting a positive power implant into the anterior chamber of a phakic eye for the treatment of hyperopia. Moreover, due to the shallowness of the anterior chamber in hyperopic eyes, surgical location of a positive power implant in the anterior chamber of the phakic eye for the treatment of hyperopia would be in contravention of, and counterintuitive to, the state of the art.

It has been generally acknowledged by those skilled in the art that there are significant risks involved with the use of anterior chamber angle supported implants in the aphakic eye (reviewed in Apple et al., in Intraocular Lenses: Evolution, Designs, Complications and Pathology (William and Wilkens, Baltimore) 1989, Chapter 4, pp. 59–105) and more so in the phakic eye (Id. at p. 65, col. 1). For example, when such an implant is inserted into the eye, temporary or permanent adhesions of the implant to iris tissue may result, causing damage to these structures to ensue either immediately or over the long term affecting pupillary mobility and contour. In addition, once the implant is in position, it may cause similar angle adhesions due to mechanical and/or chemical inflammation which may lead to fibrosis of a progressive nature. This would make subsequent removal of the implant a complex, dangerous surgical procedure. Other problems associated with such implants are cataract formation, secondary glaucoma, corneal edema, hyphema, and progressive endothelial cell loss, in addition to other complications.

As observed in Ophthalmology Alert, Vol. 1, No. 11 (Nov. 1990), pp. 41–42, Comment on page 42, several American manufacturing companies that were preparing to begin clinical trials of phakic anterior chamber ocular implants in the United States are now likely to abandon these studies, due to the attendant risks associated with anterior chamber implants in the phakic eye and the difficulty of obtaining approval of the U.S. Food and Drug Administration (FDA) for the use of the implants. A significant risk involved in the use of such anterior chamber implants in the phakic eye is the potential for the implanted lens to contact the corneal endothelium, the anatomic lens or the iris with resultant complications, even with the enhanced vault design theorized in the studies discussed in Ophthalmology Alert because such design would bring the lens optic edge quite close to the midperipheral corneal endothelium. One alternative to avoid contact with the corneal endothelium is to reduce the diameter of the optic of the minus power lens, however, such a modification creates significant drawbacks, including glare and haloing under low light conditions, ovalization of the pupil, and, as reported in Perez-Santonja et al., J. Cataract Refract Surg 22:183–187 (1996) (discussing Baikoff ZB5M), induces an inflammatory response.

It would clearly be advantageous to employ an uncoated positive power anterior chamber ocular implant that would avoid the occurrence of the above-described problems associated with anterior chamber implants for the treatment of hyperopia.

Hyperopia, a condition commonly known as farsightedness, has been known to be treated by wearing positive power eyeglasses, contact lenses, and/or surgically implanted iris supported or posterior chamber intraocular lenses. Plastic rings have also been surgically sutured to the sclera for the treatment of hyperopia and presbyopia. It was generally believed by persons of skill in the art that the anterior chamber of the phakic eye of those individuals suffering from hyperopia was more shallow than in the phakic eye of those individuals suffering from myopia. Therefore, attempts to correct hyperopia did not involve implantation of a positive power implant into the anterior chamber of the phakic eye.

U.S. Pat. No. 4,769,035 discloses a posterior chamber implant for implantation in the phakic eye for correction of hyperopia. This posterior chamber implant is designed specifically to come into immediate and direct contact with the anterior surface of the natural lens. The surgical procedure for implanting this posterior chamber implant requires a pre-implantation determination of the precise shape and contouring of the surface of the natural lens and the specific amount of optical correction required for placement of such a lens in direct contact with the natural lens.

U.S. Pat. No. 5,489,299 discloses a method of treating hyperopia and presbyopia wherein the effective working distance of the ciliary muscle can be increased by expanding the sclera in the region of the ciliary body by suturing to the sclera a relatively rigid band having a diameter slightly greater than that of the sclera in the region of the ciliary body. Rings are surgically implanted, and intraocular lenses are not used at all in this procedure.

U.S. Pat. No. 5,192,319 discloses an intraocular lens surgically positioned in the anterior chamber to be used in addition to the natural lens to correct refraction by fixation of such lens on the iris using one or more pairs of pincer-like extensions for holding the position of the lens to the iris tissue. This patent discloses a positive power implant for placement in the anterior chamber of the phakic eye for correction of hyperopia, specifically designed to attach to the iris. Although such positioning on the iris may provide for safe clearance away from vital structures such as the natural lens and the corneal endothelium, the implant has a number of significant drawbacks. Damage may occur to the sensitive iris tissue and the damage is increased when adjusting the position of the implant in cooperation with the existing lens. Also, deterioration of the iris tissue occurs, thereby decreasing the ability to place future replacement implants on the iris. Contact with vital intraocular structures may occur. The patent states at column 4, lines 25–27, that "[a]ll designs are a compromise between the anatomical limitations caused by the position of the intraocular lens in the anterior chamber and the optical requirements." In addition the disadvantages of iris mounted anterior chamber implants are discussed by Apple et al., in Intraocular Lenses: Evolution, Designs, Complications and Pathology (William and Wilkens, Baltimore) 1989 Chapter 3, pp. 45–58, which states on page 58 that such lenses have become obsolete due to numerous complications.

U.S. Pat. No. 4,871,363 also discloses a corrective intraocular lens positioned in the anterior chamber in a phakic eye for correcting high myopia wherein a leading haptic is shorter than the trailing haptic. Such a lens would necessarily be a minus power lens, even though the illustration of FIG. 3 is drawn showing what appears to be a positive power lens, because it is designed specifically for treatment of myopia. The specification of '363 does not provide any disclosure of a positive power ocular lens in a phakic eye for treatment of hyperopia since the invention is limited to the treatment of myopia. Moreover, the intraocular lens that is disclosed in the '363 patent is admitted to be designed primarily for the replacement of a natural lens in an aphakic eye at col. 3, lines 36–44. The '363 patent does not appreciate the problems associated with positive power ocular implants actually implanted into the phakic eye.

U.S. Pat. No. 4,676,792 discloses a minus power intraocular implant for placement in the anterior chamber of the phakic eye for the treatment of myopia. Although FIG. 2 of the '792 patent shows a convex anterior surface of the optic, the optic is minus power due to the concave curvature of the posterior surface of the optic. The '792 patent does not appreciate the complications associated with a planar or convex posterior surface of the optic in combination with a convex or planar anterior surface.

To Applicant's knowledge, there has not been a successful implantation of a positive power anterior chamber ocular implant angle supported in the phakic eye for the treatment of hyperopia. In view of the problems and risks encountered with the development of minus power anterior chamber intraocular lenses, it would have been unexpected for positive power anterior chamber intraocular lenses to be successfully modified for use in the phakic eye for the treatment of hyperopia.

It is an object of the present invention to provide a positive power ocular implant for placement in the anterior chamber of a phakic eye to correct refractive errors caused by hyperopia.

SUMMARY OF THE INVENTION

The invention is directed to a positive power ocular implant for placement in the anterior chamber of a phakic eye comprising a positive power artificial refracting lens having at least one convex surface and means for positioning the lens in the anterior chamber of the eye, wherein contact between the positive refracting lens and other anatomic bodies is avoided, and wherein the means for positioning avoids contact with the iris and corneal endothelium.

In one embodiment, the inventive implant has a special degree of flexure so that when pressure is applied to the implant upon surgical insertion to an eye, the haptics compress and the optic vaults in a manner wherein contact with the iris and other anatomical bodies in the eye is avoided and wherein blood supply in the anatomic angle of the eye is not cut off when the haptics are implanted therein.

In one embodiment, the implant of the present invention is uncoated. In an alternative embodiment, the inventive implant is coated with a medicament comprising a compatible sulfated polysaccharide as disclosed herein and as disclosed in U.S. patent application Ser. No. 07/745,927 filed Aug. 16, 1991, U.S. patent application Ser. No. 08/193,160 filed Aug. 25, 1994, which issued as U.S. Pat. No. 5,652,014, and U.S. patent application Ser. No. 09/063,624 filed Apr. 20, 1998, the disclosures of each are incorporated herein by reference in their entirety.

The invention is also directed to a method of correcting refractive errors caused by hyperopia in a patient in need thereof comprising surgically implanting and anchoring in the anterior chamber of a phakic eye a positive power anterior chamber ocular implant comprising a positive artificial refracting lens having at least one convex surface and a means for positioning the positive refracting lens in the anterior chamber of the eye, wherein contact between the positive refracting lens and other anatomic bodies is avoided and wherein the means for positioning the lens avoids contact with the iris and corneal endothelium. In a preferred embodiment, the implant is anchored in the anatomic angle in the anterior chamber of the phakic eye.

DETAILED DESCRIPTION OF THE INVENTION

The invention is directed to a positive power anterior chamber ocular implant of a phakic eye comprising a positive artificial refracting lens having at least one convex surface and means for positioning the lens in the anterior chamber of the eye, wherein contact between the lens and other anatomic bodies is avoided, and wherein the means for positioning avoids contact with the iris.

As used in this description and the appended claims, the term "positive power anterior chamber ocular implant" refers specifically to a positive refracting lens and means for positioning said lens which together can be surgically implanted in the phakic eye to compensate for and/or correct refractive errors and specifically excludes intraocular lenses which are surgically inserted in the aphakic eye, such as are disclosed, for example, in U.S. Pat. No. 4,240,163.

The invention is based in part on the discovery that the anterior chamber in a phakic eye of a person with hyperopia has enough room for placement of the inventive positive power anterior chamber intraocular lens. Specifically, approximately 75% of persons with hyperopia have an anterior chamber depth of at least 2.7 to 2.8 mm.

Figure 1:
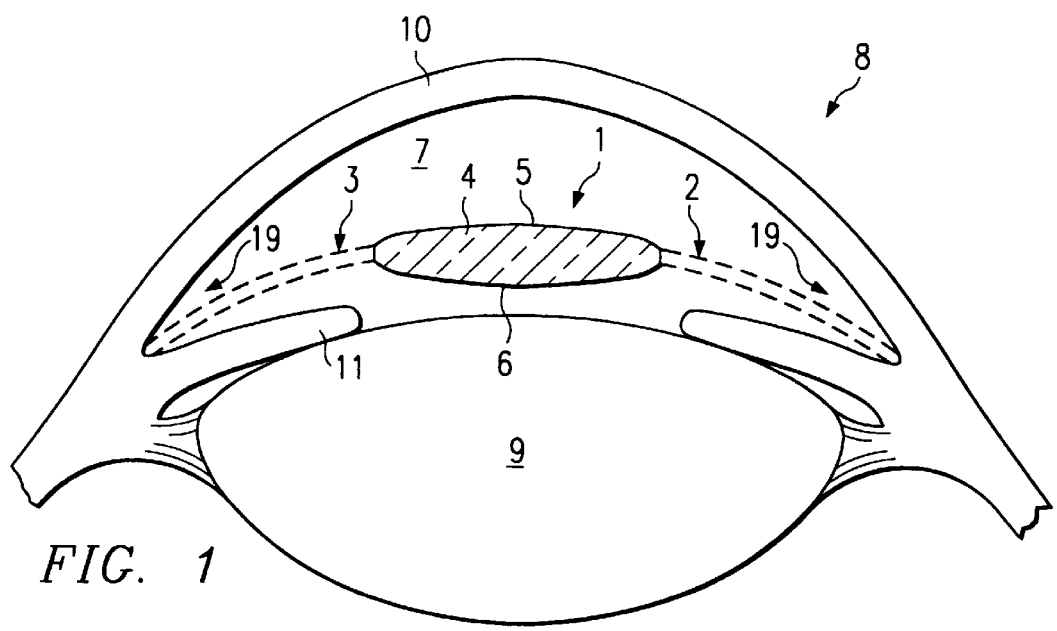
FIG. 1 is a side cross-sectional view of an eye containing a biconvex implanted anterior chamber ocular implant implanted in the angle of the eye in accordance with the present invention.

In a preferred embodiment of this invention, as depicted in FIG. 1, the representative positive power anterior chamber ocular implant 1 has two haptics 2 and 3 integral to the positive refracting lens 4, so that when implanted into the anterior chamber 7 of the eye 8, the lens 4 is positioned and maintained by the haptics to prevent contact between it and other anatomical bodies such as the anatomical lens 9, the iris 11, and the corneal endothelium 10. In this view, both the anterior surface 5 and posterior surface 6 of the lens 4 are convex. However, in alternative embodiments, the anterior surface 5 and the posterior surface 6 of the lens 4 may be concave, convex or planar, provided at least one of the surfaces 5 and 6 is convex. In a preferred embodiment haptics 2 and 3 are implanted into the anatomic angle of the eye 19.

The optical portion of the uncoated refractive implant employed in the present invention, commonly referred to as the lens or optic 4, is preferably fabricated from compounds such as polymethylmethacrylate, poly-2-hydroxyethylmethacrylate, methylmethacrylate copolymers, siloxanylalkyl, fluoroalkyl and aryl methacrylates, silicone, silicone elastomers, polysulfones, polyvinyl alcohols, polyethylene oxides, copolymers of fluoroacrylates and methacrylates, and polymers and copolymers of hydroxyalkyl methacrylates, such as 2-hydroxymethyl methacrylate, glyceryl methacrylate, 2-hydroxypropyl methacrylate, as well as methacrylic acid, acrylic acid, acrylamide methacrylamide, N,N-dimethylacrylamide, and N-vinylpyrrolidone. The artificial refracting lens 4 of the present invention may be foldable or rigid depending upon the particular selected composition of the lens.

The positive refracting lens of the inventive implant has a lens shape with two refractive surfaces, an anterior and posterior surface, such that the combined refractive powers of the two surfaces is a plus or positive. Lenses having at least one convex surface are typically employed to correct hyperopia. The other surface may be planar, convex or concave. In a specific non-limiting embodiment, the anterior surface 5 is convex; and in an alternative embodiment the posterior surface 6 is convex.

It is well known to those skilled in the art that when positioning an implant within the anterior chamber of the phakic eye, it is important to avoid, inter alia, contact between the implant and the anatomic lens residing in the posterior chamber. In the present invention, the vault and sagitta values of the implant and means for positioning the optical portion of the implant in the anterior chamber of the eye to prevent such contact with other anatomic bodies are integral. The vault is measured in relation to a flat surface upon which the haptics may rest and the posterior surface of the optic, when the implant is in a resting position or implanted in the eye. The sagitta is measured in relation to a flat surface upon which the haptics may rest and the anterior surface of the optic, when the implant is in a resting position or implanted in the eye.

In a specific embodiment, the means for positioning the implant in the anterior chamber of the phakic eye are haptics designed to anchor the implant in the anatomic angle of the eye. According to the present invention the haptics may have any configuration. In a preferred embodiment, each haptic has an "S" configuration illustrated in FIG. 2, the outer portion of the "S" configuration 15 of the haptic is concave in relation to the angle recess contact to allow solely for a four-point attachment 20 of the haptics and to prevent haptic angle contact with its consequent synechia formation and pupillary distortion. This backward curvature 15 of the haptics should be within the outer flat contact plane as also seen in FIG. 2.

Figure 2:
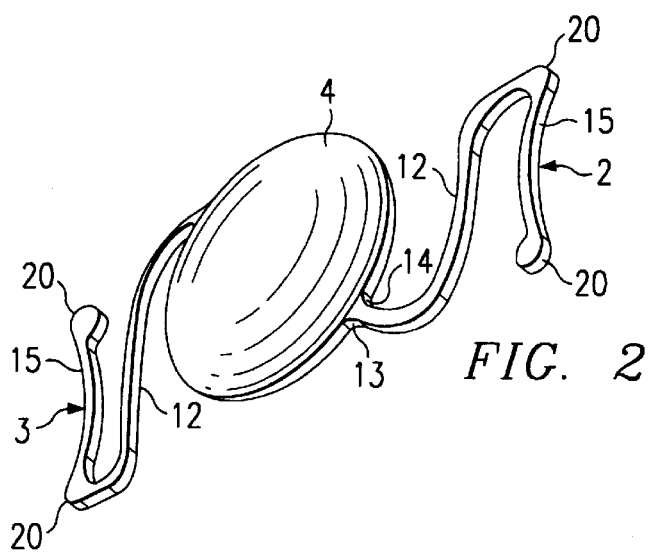
FIG. 2 shows a top planar view of one embodiment of an anterior chamber ocular implant in accordance with the present invention, wherein the positive refracting lens is biconvex.
Figure 3:
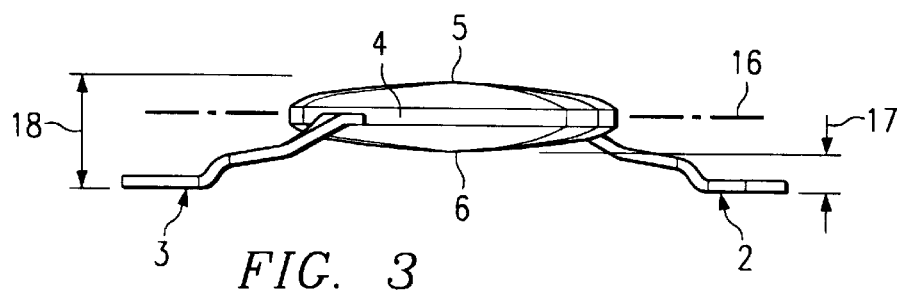
FIG. 3 shows a sideview of the embodiment of FIG. 2.

As illustrated in FIGS. 2 and 3, the haptics 2 and 3 should suspend the lens 4 in the anterior chamber of the eye at a vault 17 between the range of 0.8 mm to 1.2 mm, preferably 1.0 mm, to prevent contact of the positive refracting lens with the natural crystalline lens or iris as shown in FIG. 3. A sagitta value representing a minimal displacement of the optic is preferred. Maximum sagitta 18 values range between 1.2 mm to 1.75 mm.

Further, the haptics preferably are made of highly flexible material having varying degrees of curvature. The haptics may be made of the same material as described above for the optical portion of the implant, or may be made of materials such as polypropylene. Depending on the composition selected, flexure of the haptics may be varied.

In a preferred embodiment, compression of the haptics is achieved through a structural design of the haptics having an intermediate beam 12 length of approximately 5.25 mm, as shown in FIG. 2, such that when the haptic moves inward, the outer diameter decreases, and the change in the vault is limited. It has been discovered that a long beam length decreases the ratio between vault and compression. A unique flexure of the implant in accordance with the present invention is obtained by lengthening the intermediate beam length and thinning the transition between the haptic and the optic, which reduces axial displacement during compression. The long intermediate beam dramatically reduces the compression force transmitted to the tissue in the angle, blood supply to the anatomic angle is not cut off, and subsequent necrosis of angle tissue is avoided so as not to distort iris' architecture.

In a further preferred embodiment, each haptic is designed normal to the optic 13 and 14, as shown in FIG. 2, and has no blend zone or bumps at all. This transition maximizes beam length, places all torques on the same line so that a stable couple is created reducing tilt, and markedly reduces adverse optical transients and torque/tilt transients which could result in serious damage to the eye. The transition further reduces glare effects, allows for the optic diameter to be large with a maximum overall distance, and reduces optic mass.

The haptic design having a long intermediate beam length and the haptic design normal to the optic each contribute to a reduced risk of endothelial cell damage, a reduced risk of damage to the natural lens during and after surgical implantation in the anterior of a phakic eye, a reduced glare and haloing, and a reduced ovaling of the pupil.

As seen in FIG. 2, the transition between the haptic and the optic body occurs smoothly in a concave manner without any kind of hump or bump effect and without any blending or connecting zone between each haptic 2 and 3 and the optic 4 (i.e. the haptic entry is normal to the optic) as shown at 13 and 14. Further, each haptic 2 and 3 is attached to the optic 4 so that each haptic is angled in a manner that it is not perpendicular to the optic 4, as seen in FIG. 3. Position line 16 represents a position wherein the haptics would be perpendicular to the optic if they were attached along that line. The blend radius (i.e. degree of curvature) of the haptics where the haptic transitions with the optic is between 0.1 mm at a minimum and 0.4 mm, wherein a smaller blend radius is preferred. In both the horizontal plane and vertical plane, the blend radius between the optic and each haptic is preferably at right angles. However, because a right angle may not be achievable with conventional machinery, a 0.2 mm blend radius is presently the preferred working embodiment.

The haptics are designed having an intermediate beam 12 length of approximately 5.25 mm allowing the haptic to compress with a limited change in vault. Additionally, an increased elasticity of the haptic by thinning the haptic at the transition between the haptic and the optic to a thickness between the range of 0.25 mm to 0.35 mm in combination with increasing the intermediate beam length helps to limit vault changes and reduce compression force. Moreover, a vault value between the range of 0.8 to 1.2 with a maximum sagitta value between the range of 1.3 mm to 1.75 mm, insures that any limited changes in vault that may occur will not inflict damage to other anatomic bodies. In a preferred embodiment, the means for positioning the lens are haptics that compress about 1 mm and the vault of the optic of the anatomic lens is limited to about 0.1 mm. The haptic design precludes necrosis of angle tissue and does not to distort the iris' architecture.

Positive power anterior chamber ocular implants made in accordance with the present invention have an overall omega value of 12–14 mm and an optical diameter of 5 to 7 mm. An omega value is the overall diameter of a container into which the implant may be placed. The center thickness of the optical portion of the implant may be in the approximate range of between 0.2 mm to 0.52 mm in the center of the optic and 0.1 mm to 0.3 mm around the periphery of the optic, which ranges vary with the degree of power.

In an alternative, non-limiting embodiment, the positive power anterior chamber ocular implant of the present invention may be coated. The coating may comprise any compatible sulfated polysaccharide medicament. This coating is preferably selected from the group consisting of heparin, heparin sulfate, chondroitin sulfate, dermatan sulfate, chitosan sulfate, xylan sulfate, dextran sulfate, and sulfated hyaluronic acid. Heparin is particularly preferred for use as the coating, with heparin having a molecular weight in the range of about 2,500–15,000 daltons. Commercially available heparin, which usually has a molecular weight of from about 12,000 to about 15,000 daltons, may lead to platelet agglutination. Consequently, lower molecular weight heparin (a derivative or fraction) may be more suitable in the range of molecular weight of from about 2,500–10,000, most preferably about 2,500–5,300 daltons and even somewhat higher. These low molecular weight heparins can be prepared by enzymatic hydrolysis or depolymerization of heparin with heparinase as disclosed, for example, by U.S. Pat. No. 3,766,167, or by depolymerizing either heparin residues or commercial porcine or bovine heparin by reacting the heparin material with a blend of ascorbic acid and hydrogen peroxide, the reaction products then being isolated and fractionated by precipitation using an organic solvent, such as ethanol, methanol, acetone, or methyl ethyl ketone. Commercially available heparin may also be cleaved chemically using nitrous acid to yield lower molecular weight heparin, including heparin having a molecular weight in the range of about 2500–10,000 daltons, preferably 2500–5300 daltons.

The coating of the implant may be bonded to the surface of the implant by any method of bonding well known by those skilled in the art, for example, in accordance with U.S. Pat. No. 5,652,014, and preferably in such a manner that the coating is bonded to the surface of the implant by means of covalent bonding, ionic bonding, or hydrogen bonding, with covalent bonding being particularly preferred.

Alternatively, the implant surface is first treated with a plasma to generate an amine-containing surface, a carboxylic acid containing-surface, or an active or passive free radical-containing surface, and heparin compounds or derivatives thereof are thereafter employed to coat the implant surface.

In a preferred non-limiting embodiment, the implant surface is coated with a biocompatible polysaccharide medicament by way of end-group attachment to the implant.

The method of coating the medicament-coated implant of this invention may be any appropriate well known coating technique, such as immersion coating, spray coating and the like, using a suitable solution or dispersion of the medicament dissolved or dispersed in an appropriate solvent or dispersant, such as water, ethanol, and the like, with the solvent not affecting the optics of the lens material. The coating solution or dispersion has a conventional concentration of medicament which corresponds to the particular coating technique selected. Typically, after the coating is applied to the implant, it is dried, for example, by drying at room temperature or above. The coating may be repeatedly applied, if necessary, to achieve the desired coating weight or thickness. The coating should not affect the transmission of visual light, and typically has a thickness in the range of from about $1/100,000$ mm to $1/100$ mm, and constitutes from about $1/10,000\%$ to about $1/10\%$ by weight of the implant.

Additional medicaments and other compounds may also be employed in conjunction with the compatible sulfated polysaccharide medicament coating of the present invention. For example, in one embodiment the coating is additionally complexed with antithrombin to provide the coated implant with anticoagulation properties.

Additionally, compounds which absorb ultraviolet or other short wavelength (e.g. below about 400 nm) radiation, such as compounds derived from benzotriazole groups, benzophenone groups, or mixtures thereof may be added to the monomers and/or polymers which constitute the anterior chamber ocular implant. Other compounds well known to those skilled in the art may also be used in fabricating the anterior chamber ocular implant employed in this invention.

EXAMPLE 1

Representative uncoated positive power ocular implants were made from polymethylmethacrylate ("PMMA") each comprising an optic having a diameter of 6 mm and an omega value of 13 mm. The center thickness (TC) of the optical portion of each implant is shown in Table 1 below. The edge thickness (TE) of each optic was held constant at 0.220 mm. The posterior surface (RP) of each optic was kept planar. The anterior surface (RA) of each optic was convex, each having a degree of curvative shown in Table 1 below. The vault of each optic was set at 1.0 mm. The resulting degree of positive refraction is shown for each optic as indicated by its diopter value. The sagitta values of each provided optic are provided in Table 1. The haptics of each optic are made of PMMA and are in a four point "S" configuration. Each haptic has an intermediate beam length of 5.25 mm. The transition between the haptic and optic is normal to the optic, having a blend radius ranging in the horizontal and vertical plane between 0.1 and 0.2. Each of the haptics have been thinned to a thickness between the range of 0.25 mm to 0.35 mm. The implants were each tumble polished until fully smooth.

TABLE 1

| Implant | TE (mm) | TC (mm) | RA (mm) | RP | Diopter | Vault (mm) | Sagitta |
|---|---|---|---|---|---|---|---|
| 1 | .220 | 0.511 | 15.600 | planar | 10.0 | 1.0 | 1.511 |
| 2 | .220 | 0.496 | 16.421 | planar | 9.5 | 1.0 | 1.496 |
| 3 | .220 | 0.482 | 17.333 | planar | 9.0 | 1.0 | 1.482 |
| 4 | .220 | 0.467 | 18.353 | planar | 8.5 | 1.0 | 1.467 |
| 5 | .220 | 0.452 | 19.500 | planar | 8.0 | 1.0 | 1.452 |
| 6 | .220 | 0.437 | 20.800 | planar | 7.5 | 1.0 | 1.437 |
| 7 | .220 | 0.423 | 22.286 | planar | 7.0 | 1.0 | 1.423 |
| 8 | .220 | 0.408 | 24.000 | planar | 6.5 | 1.0 | 1.408 |
| 9 | .220 | 0.394 | 26.000 | planar | 6.0 | 1.0 | 1.394 |
| 10 | .220 | 0.379 | 28.364 | planar | 5.5 | 1.0 | 1.379 |
| 11 | .220 | 0.365 | 31.200 | planar | 5.0 | 1.0 | 1.365 |
| 12 | .220 | 0.350 | 34.667 | planar | 4.5 | 1.0 | 1.350 |
| 13 | .220 | 0.336 | 39.000 | planar | 4.0 | 1.0 | 1.336 |
| 14 | .220 | 0.321 | 44.571 | planar | 3.5 | 1.0 | 1.321 |
| 15 | .220 | 0.307 | 52.000 | planar | 3.0 | 1.0 | 1.307 |
| 16 | .220 | 0.292 | 62.400 | planar | 2.5 | 1.0 | 1.292 |
| 17 | .220 | 0.278 | 78.000 | planar | 2.0 | 1.0 | 1.278 |

EXAMPLE 2

Representative implants of Table 1 were then tested for compression force, axial displacement, decentration, contact angle and optic tilt. Eighteen implants were made according to the specifications of Implant 1, described above in Example 1. Implants were exposed to a 0.5 mm diametral compression and a 1.0 mm diametral compression. The resulting mean and standard deviation values measured in grams are shown in Table 2 below.

TABLE 2

| | Diametral Compression of 0.5 mm | | Diametral Compression of 1.0 mm | |
|---|---|---|---|---|
| | mean | std dev | mean | std dev |
| Compression Force | 0.158 | 0.031 | 0.459 | 0.082 |
| Axial Displacement | 0.112 | 0.018 | 0.245 | 0.030 |
| Decentration | 0.082 | 0.043 | 0.122 | 0.077 |
| Contact Angle | 6.657 | 0.051 | 6.694 | 0.085 |
| Optic Tilt | 0.987 | 0.506 | 0.719 | 0.447 |

EXAMPLE 3

The present invention is further directed to a method of correcting refractive errors caused by hyperopia by way of surgically implanting and anchoring a positive power anterior chamber ocular implant in the anterior chamber of the phakic eye in a subject in need thereof, wherein the positive artificial refracting lens has at least one convex surface and a means for positioning the positive refracting lens in the anterior chamber of the eye. By this method contact between the positive refractings lens and other anatomic bodies is avoided and the means for positioning the lens in the anterior chamber avoids contact with the iris and corneal endothelium.

Implants made in accordance with the present invention were surgically implanted into subjects having a natural lens in situ and anchored in the anatomic angle of the anterior chamber of the eye, according to traditional surgical techniques. The subjects were studied for inflamation and damage to the eye post insertion. No inflamation or damage occurred upon surgical implantation and anchoring, and no latent damage was subsequently observed. No subjects experienced ovaling of the pupil or haloing in low light conditions, and none required removal of the positive power anterior chamber ocular implants.

The invention described and claimed herein is not to be limited in scope by the specific embodiments herein disclosed which are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

I claim:

1. A positive power anterior chamber ocular implant for placement in the anterior chamber of a phakic eve comprising a positive artificial refracting lens having at least one convex surface and a means for positioning the lens in the anterior chamber of the eye, wherein contact between the positive refracting lens and other anatomic bodies is avoided, wherein the means for positioning avoids contact with the iris and corneal endothelium, and wherein the positive refracting lens has two convex surfaces.

2. The implant according to claim 1, wherein the positive refracting lens has a convex posterior surface.

3. A positive power anterior chamber ocular implant for placement in the anterior chamber of a phakic eve comprising a positive artificial refracting lens having at least one convex surface and a means for positioning the lens in the anterior chamber of the eye, wherein contact between the positive refracting lens and other anatomic bodies is avoided, wherein the means for positioning avoids contact with the iris and corneal endothelium, wherein the means for positioning the lens in the anterior chamber of the eye to prevent contact between the implant and the anatomic lens comprises two haptics wherein each haptic is normal to the positive artificial refracting lens, wherein each haptic has an intermediate beam length of approximately 5.25 mm, and wherein the haptics suspend the artificial lens in the anterior chamber of the eye at a vault of approximately 08. mm to 1.2 mm with a sagitta of approximately 1.3 mm to 1.75 mm.

4. The implant according to claim 3, wherein the haptics compress about 1 mm and the vault of the optic is about 0.1 mm.

5. A method of correcting refractive errors caused by hyperopia in a patient in need thereof comprising surgically implanting and anchoring in an anterior chamber of a phakic eye having an anatomic angle a positive power anterior chamber ocular implant comprising a positive artificial refracting lens having at least one convex surface and a means for positioning the positive refracting lens in the anterior chamber of the eye, wherein contact between the positive refracting lens and other anatomic bodies is avoided and wherein the means for positioning the lens avoids contact with the iris and corneal endothelium.

6. The method according to claim 5, wherein the means for positioning the lens comprises haptics.

7. The method according to claim 6, wherein the haptics are anchored in the anatomic angle in the anterior chamber of the eye.

8. The method according to claim 7, wherein the haptics have an intermediate beam length of 5.25 mm.

9. The method according to claim 7, wherein the haptics are normal to the positive artificial refracting lens.

10. The method according to claim 8, wherein the haptics are normal to the positive artificial refracting lens.

* * * * *